(12) United States Patent
Geisendoerfer et al.

(10) Patent No.: US 7,294,240 B2
(45) Date of Patent: Nov. 13, 2007

(54) METHOD FOR PRODUCING (METH)ACRYLIC ACID ESTERS

(75) Inventors: Matthias Geisendoerfer, Neustadt (DE); Gerhard Nestler, Vienna (AT); Juergen Schroeder, Ludwigshafen (DE); Hugues Vandenmersch, Wachenheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 313 days.

(21) Appl. No.: 10/479,962

(22) PCT Filed: May 28, 2002

(86) PCT No.: PCT/EP02/05818

§ 371 (c)(1),
(2), (4) Date: Dec. 8, 2003

(87) PCT Pub. No.: WO02/100817

PCT Pub. Date: Dec. 19, 2002

(65) Prior Publication Data

US 2004/0168903 A1    Sep. 2, 2004

(30) Foreign Application Priority Data

Jun. 8, 2001    (DE) ................. 101 27 938

(51) Int. Cl.
*B01D 3/34* (2006.01)
*C07C 213/06* (2006.01)
*C07C 213/10* (2006.01)
*C07C 51/44* (2006.01)
*C07C 67/54* (2006.01)

(52) U.S. Cl. .............. 203/6; 203/29; 203/49; 203/71; 203/99; 203/DIG. 19; 203/DIG. 21; 203/DIG. 25; 560/218; 560/222; 562/600

(58) Field of Classification Search ............ 203/4, 203/6, 29, 49, 99, 71, DIG. 19, DIG. 21, 203/DIG. 25; 560/222, 218; 562/600
See application file for complete search history.

(56) References Cited

U.S. PATENT DOCUMENTS

| | | | |
|---|---|---|---|
| 2,832,800 A | | 4/1958 | Specht et al. |
| 3,816,267 A | * | 6/1974 | Chuang .................. 203/8 |
| 4,147,721 A | * | 4/1979 | Leacock .............. 562/532 |
| 4,260,821 A | * | 4/1981 | Benjamin ............ 562/532 |
| 4,698,440 A | * | 10/1987 | Blair et al. ........... 560/205 |
| 6,232,435 B1 | * | 5/2001 | Heitz et al. .......... 528/491 |
| 6,334,935 B1 | * | 1/2002 | Uehara et al. .......... 203/8 |
| 6,417,392 B1 | * | 7/2002 | Nagano et al. ....... 560/222 |
| 6,437,173 B1 | * | 8/2002 | Hurtel et al. ........ 560/217 |
| 6,482,976 B1 | * | 11/2002 | Ho et al. ............. 560/205 |
| 6,818,791 B2 | * | 11/2004 | Martin et al. ........ 560/205 |
| 7,026,503 B2 | * | 4/2006 | Nestler et al. ........ 560/217 |

FOREIGN PATENT DOCUMENTS

| | | |
|---|---|---|
| DE | 1 067 806 | 10/1959 |
| DE | 12 48 943 | 8/1967 |
| DE | 2 008 618 | 9/1970 |
| DE | 28 05 702 | 8/1978 |
| DE | 40 19 788 | 1/1992 |
| DE | 101 27 939 | 5/2002 |
| EP | 0 160 427 | 11/1985 |
| EP | 0 298 867 | 7/1988 |
| EP | 0 376 088 | 7/1990 |
| EP | 0 906 902 | 4/1999 |
| EP | 0 960 877 | 12/1999 |
| FR | 2 617 840 | 7/1987 |
| JP | 3-112949 | 5/1991 |

OTHER PUBLICATIONS

Organikum, vol. 17 Veb DL Verlag der Wissenschaften, Berlin p. 506, 1988.

* cited by examiner

*Primary Examiner*—Virginia Manoharan
(74) *Attorney, Agent, or Firm*—Oblon, Spivak, McClelland, Maier & Neustadt, P.C.

(57) ABSTRACT

Basic (meth)acrylates IV are prepared by transesterification of alkyl (meth)acrylates I in the presence of a catalyst and working-up of the reaction mixture by distillation, by a process in which a gas or gas mixture which is inert under the reaction conditions is passed through the reaction zone and/or heat exchanger.

15 Claims, No Drawings

METHOD FOR PRODUCING (METH)ACRYLIC ACID ESTERS

TITLE OF THE INVENTION

Preparation of (meth)acrylates

BACKGROUND OF THE INVENTION

1. Field of the Invention

The present invention describes a process for the preparation of basic (meth)acrylates (IV) in high purity and with a high yield by transesterification of an industrial lower alkyl (meth)acrylate I with basic alcohols ($R^2OH$).

2. Description of the Background

High purity is understood as meaning a purity of at least 99.8%, the total content of saturated impurities (without water) being not more than 1000 ppm and the content of N,N'-dimethylpiperazine, ethylene glycol di(meth)acrylate and vinyloxyethyl (meth)acrylate being not more than 100 ppm in each case.

(Meth)acrylates are useful starting compounds for the preparation of polymers and copolymers which are used, for example, as finishes, dispersions or adhesives.

Saturated impurities, i.e. those which have no carbon-carbon multiple bonds, e.g. alcohols, ethers and acetic and propionic acid derivatives, are disadvantageous in that they withstand the polymerization unchanged, i.e. are not incorporated into the polymer, and may lead to the product having an annoying odor. In order to separate off the residual volatile components, for example from dispersions, expensive treatments (deodorizations) are additionally required.

As a rule, a treatment referred to as physical deodorization is carried out and comprises stripping the dispersion with steam, air or nitrogen in a stirred container (German Published Application DAS 12 48 943) or in a counter current column. The treatment is carried out in one or more stages, depending on the amount and the boiling points of the components to be separated off. The removal of these impurities is accordingly an expensive procedure, which moreover cannot be carried out in the case of heat-sensitive dispersions owing to the thermal stress.

The content of ether (dibutyl ether is entrained, for example, with butyl acrylate as lower (meth)acrylate I, see below) also has an adverse effect if the procedure is carried out in the presence of oxygen-containing gases, such as air, for example for stabilization. It is known that, in the presence of oxygen, ethers very readily form peroxides and it is known that these may then initiate a polymerization of (meth)acrylate compounds, which may even take place explosively.

The ether content is accordingly not only a quality problem but also a safety problem.

Ethylene glycol di(meth)acrylate and vinyloxyethyl (meth)acrylate, which occur as secondary components in the preparation of alkylaminoethyl (meth)acrylates, contain two unsaturated groups and therefore act as crosslinking agents in the polymerization. This is extremely disadvantageous since consequently the polymerization and the quality of the polymers are adversely affected, for example by gel formation. In addition, they influence the shelf-life.

The preparation of basic (meth)acrylates IV by transesterification of lower (meth)acrylates I with basic alcohols $R^2OH$ is generally known.

It is furthermore generally known that the transesterification is an equilibrium reaction. In order to achieve economical conversions, the resulting lower alkanol $R^1OH$, being the component with the lowest boiling point, is therefore generally removed continuously from the equilibrium by distillation, a very pure alkanol fraction being desirable for economic reasons in order to be able to use it again, for example in the preparation of the lower (meth)acrylate I by esterification. Owing to the position of the boiling points and formation of azeotropic mixtures, however, this distillate generally does not consist of pure lower alkanol $R^1OH$ but is contaminated with the lower (meth)acrylate I and possibly with basic alcohol $R^2OH$.

Since, for economic reasons, it is expedient to utilize the distillate, impurities have an adverse effect, particularly when they are basic impurities, i.e. compounds having an amino group.

The particularly economical recycling to the synthesis of the lower ester is especially influenced thereby, cf. for example EP-A2 906 902, page 3, lines 4-16.

EP-A2 906 902 describes a process for the preparation of alkylamino (meth)acrylates by transesterification of alkyl (meth)acrylates with alkylaminoalcohols in the presence of a catalyst, e.g. dibutyltin oxide, in which the alcohol-containing distillate (azeotropic mixture) is passed, either directly or after a further distillation, over an acidic ion exchange resin. The basic nitrogen-containing impurities from the distillate are bound by the acidic groups and thus separated from the alkanol/(meth)acrylate mixture, which can then be used again in the synthesis of the lower (meth)acrylate. The working-up of the transesterification mixture is carried out in a plurality of distillation stages, the additional formation of the Michael adducts during the catalyst removal being reduced as far as possible.

Michael adducts are defined as the compounds formed by addition of alcohols at the double bond of the (meth)acrylates.

It is generally known that this addition (cf. equation I) takes place in particular in the presence of alkaline catalysts (Organikum, 17th Edition, page 506, VEB Deutscher Verlag der Wissenschaften, Berlin 1988).

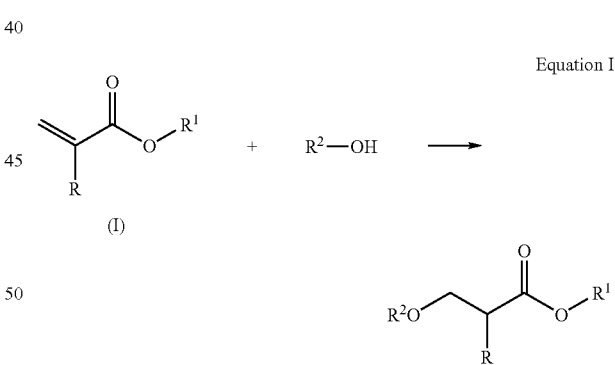

Equation I

By means of a two-stage catalyst removal (EP-A2 906 902, page 4, lines 51-57), the additional formation (ratio of increase) of the Michael adducts is kept below 2%. According to examples III-1, III-2 and III-3, the distillation temperatures and the residence times play a decisive role. On increasing the temperature in stage 2 or the residence time in both stages, the ratio of increase of the Michael adducts does in fact increase substantially (from 0.48 to 0.96 and 2.2%, respectively).

The actual, absolute content of the Michael adducts in the reaction mixture, which is decisive for the yield and the cost-efficiency of the process, is mentioned nowhere in EP-A 906 902.

The process has the following disadvantages:
1. Necessity of purification using an ion exchanger.
2. The regeneration and disposal of the exchange resin laden with the basic impurities is expensive and environmentally polluting.
3. It requires from 5 to 7 distillation steps and is thus technically complicated.
4. The yield is low (about 33%, example III-1).
5. The amino alcohol must be metered in continuously over a long period (4 hours, cf. example III-1) in order to reduce the formation of the Michael products.
6. Long reaction times are required (7-8 hours) which reduces the cost-efficiency.

Our own investigations have shown that in particular the reaction time (i.e. the residence time in the reactors) has a decisive effect on the formation of the Michael adducts (cf. example 3). On the other hand, the temperature and the residence time in the catalyst removal surprisingly are of no importance for the formation of the Michael adducts in the novel process (cf. comparative examples 1 and 2).

As a rule, methyl and ethyl (meth)acrylate are used as starting materials in the transesterification (EP-A 960 877, FR 2 617 840), whereas butyl (meth)acrylate is regarded as being disadvantageous owing to its high boiling point (U.S. Pat. No. 2,832,800, column 2, lines 60-70).

Since the literature on the transesterification of alkyl (meth)acrylates provides no detailed information about the accompanying substances and impurities in the starting esters used, it must be assumed that the purity of the (meth)acrylates used is very high and no troublesome components are present.

However, the use of esters of high purity is disadvantageous since they have to be purified in a technically complicated manner by distillation after their preparation. In view of the generally known high tendency of (meth) acrylate compounds to polymerize under thermal stress, this is particularly disadvantageous.

In particular, titanium alcoholates whose alkyl groups are $C_1$- to $C_4$-alkyl radicals, e.g. tetramethyl, tetraethyl, tetraisopropyl, tetrapropyl, tetraisobutyl and tetrabutyl titanates, are proposed as catalysts for the preparation of (meth) acrylates by transesterification (cf. for example EP-B1 298 867, EP-A2 960 877). Inter alia, titanium phenolates (German Laid-Open Application DOS 200 86 18), metal chelate compounds of, for example, hafnium, titanium, zirconium or calcium, alkali metal and magnesium alcoholates, organic tin compounds or calcium and lithium compounds, for example oxides, hydroxides, carbonates or halides thereof, are furthermore proposed as catalysts.

For economic and ecological reasons, in particular alkyl titanates are used, although they are, for example, sensitive to even traces of water and some titanium alcoholates are unstable at relatively high temperatures. The result is fouling (see below) of the apparatus walls.

Furthermore, it is generally known that alkyl titanates promote the polymerization of (meth)acrylates and may therefore give rise to the formation of polymer during the transesterification and the working-up of the transesterification mixture (German Laid-Open Application DOS 20 08 618, page 3, German patent 1,067,806, column 1, lines 39-41).

Another disadvantage is that, because their activity is relatively low in some cases, titanium alcoholates necessitate high transesterification temperatures in order to achieve economical conversions or reaction times (EP-A 160 427, page 2, lines 23-32). This in turn can lead to increased polymer formation and fouling.

Another problem is the loss of activity suffered by titanium alcoholates in the course of time (German Laid-Open Application DOS 28 05 702, page 5, lines 12-21). In order to achieve economical conversions, the amount of catalyst must be increased and/or the reaction time lengthened. In view of the instability of the titanates and the byproduct and polymer formation, this is known to be disadvantageous.

Added to this is the fact that (meth)acrylic acid compounds have a considerable tendency to polymerization, very particularly if heat acts on them. Especially on the preparation and the distillative purification, they are exposed to temperatures which can easily initiate an undesired polymerization. The use of polymerization inhibitors, as is generally recommended, also cannot completely prevent the polymer formation.

Soiling of the apparatuses, blockage of pipes and pumps and fouling of column trays and heat exchanger surfaces are as a rule the result of polymer formation. The cleaning of the plants is a complicated, expensive and environmentally polluting process, and the yield and the availability of the plants (run time) are also greatly reduced as a result.

JP-A 3-112 949 describes a process for the preparation of dimethylaminoethyl acrylate by transesterification of n-butyl acrylate with dimethylaminoethanol using tetra-n-butyl titanate, in which the purification of the reaction mixture is effected in the absence of oxygen.

However, the yields of less than 90% are a disadvantage of this process.

SUMMARY OF THE INVENTION

It has now been found that the abovementioned problems in a process for the preparation of basic (meth)acrylates IV by transesterification of alkyl (meth)acrylates I in the presence of a catalyst and working-up of the reaction mixture by distillation are reduced if a gas or gas mixture which is inert under the reaction conditions is passed through the reaction zone and/or heat exchanger.

DETAILED DESCRIPTION OF THE PREFERRED EMBODIMENTS

The reaction can be represented by equation II:

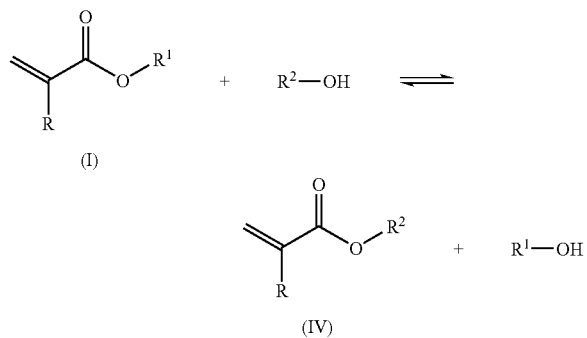

Here,

R is hydrogen or methyl, $R^2$ is a straight-chain or branched, saturated or unsaturated alkyl radical comprising two to twelve carbon atoms and substituted by at least one $NR^3{}_2$ group and $R^3$ is a straight-chain or branched, saturated or unsaturated alkyl radical comprising two to six carbon atoms, it being possible for N with the substituents $R^3$ also to form a five- to seven-membered ring and for the substituents $R^3$ to be identical or different.

$R^1$ should contain at least one carbon atom less than $R^2$.

Lower alkyl (meth)acrylate I is, for example, a (meth) acrylate of an alcohol of one to six carbon atoms, e.g. of methanol, ethanol, isopropanol, n-propanol, n-butanol, isobutanol, sec-butanol, tert-butanol, n-pentanol or n-hexanol, preferably of methanol, ethanol or n-butanol, particularly preferably of n-butanol. n-Butyl acrylate is particularly preferred.

Preferred basic alcohols $R^2OH$ are 2-dimethylaminoethan-1-ol, 3-dimethylaminopropan-1-ol, 1-dimethylaminopropan-2-ol, 2-dimethylaminopropan-1-ol, 6-dimethylaminohexan-1-ol, 2-diethylaminoethan-1-ol, 3-diethylaminopropan-1-ol, 6-diethylaminohexan-1-ol, 2-dibutylaminoethan-1-ol, 3-dibutylaminopropan-1-ol and 6-dibutylaminohexan-1-ol, said dialkylaminoethanols being particularly preferred, especially 2-dimethylaminoethan-1-ol.

Here, high purity is understood as meaning a purity of at least 99.8%, the total content of saturated impurities (without water) being not more than 1000 ppm, preferably up to 500 ppm, and that of N,N'-dimethylpiperazine, ethylene glycol di(meth)acrylate and vinyloxyethyl (meth)acrylate being not more than 100, preferably not more than 50, particularly preferably not more than 20, in particular not more than 10, ppm in each case.

Industrial alkyl acrylate and industrial alkyl methacrylate are understood as meaning the lower (meth)acrylates I produced on an industrial scale and having, as a rule, a purity of 99.0-99.8%. These (meth)acrylates contain as impurities substantially dialkyl ether (0.01-0.2%), alkyl acetate (0.01-0.1%), alkyl propionate (0.02-0.1%), alkanol $R^1OH$ (0.01-0.05%), water (0.01-0.05%), (meth)acrylic acid (0.001-0.1%) and others, e.g. isomeric alkyl acrylates (0.01-0.3%).

The novel process is described below by way of example for n-butyl acrylate as I without being restricted to it and can be applied in an analogous manner also to lower alcohols $R^1OH$ other than n-butanol, for example $C_1$- to $C_6$-alcohols, e.g. methanol, ethanol, isopropanol, n-propanol, isobutanol or n-pentanol. For this purpose, the relevant alcohol or the relevant lower (meth)acrylate I is used instead of n-butanol, the operating parameters being adapted to the changed boiling points and other physical properties of the starting materials and products, which is possible on the basis of experiments conventional in the field.

The novel process can in principle also be applied in an analogous manner to methacrylates.

The lower (meth)acrylate I is used in the novel process in industrial purity, as stated at the outset.

The lower (meth)acrylate I used in the transesterification generally has, in industrial purity, a composition as described above.

Of course, a lower (meth)acrylate I having a higher purity, for example up to 99.95% by weight, can also be used, in which case the other impurities are present in a correspondingly smaller amount.

The higher alcohol $R^2OH$ usually has a purity of at least 99.0% by weight and a water content of 0.01-0.2% by weight.

The ethylene glycol content in the case of dialkylaminoethanols as higher alcohol $R^2OH$ should be not more than 100 ppm, preferably not more than 50 ppm, particularly preferably not more than 20 ppm, in particular not more than 10 ppm. The vinyloxyethanol content in the higher alcohol $R^2OH$ should be not more than 100 ppm, preferably not more than 50 ppm, particularly preferably not more than 20 ppm, in particular not more than 10 ppm.

Dialkylaminoethanols may also contain traces, for example up to 200 ppm, preferably less than 100 ppm, of higher homologs.

The N,N'-dimethylpiperazine content is as a rule not more than 100 ppm, preferably not more than 50 ppm, particularly preferably not more than 20 ppm, in particular not more than 10 ppm.

Mixtures of higher alcohols may also be used for the transesterification.

The transesterification can be carried out in a manner known per se, for example as follows:

The lower (meth)acrylate I, preferably the methyl, ethyl or n-butyl ester, particularly preferably the n-butyl ester, is reacted with the higher alcohol $R^2OH$ in a molar ester:alcohol ratio of 1:1-4:1 in the presence of at least one catalyst.

The transesterification can be carried out batchwise, semicontinuously or continuously, preferably continuously.

For the novel process, it is possible to use all transesterification catalysts described in the prior art, preferably titanium, magnesium or aluminum alcoholates, particularly preferably titanium alcoholates, in particular titanium alcoholates of the alcohols present in the transesterification, $R^1OH$ and $R^2OH$.

If the titanium catalyst used is a lower alcoholate which does not contain the alcohol component $R^1OH$, in a preferred embodiment the catalyst is prepared beforehand as follows:

A lower titanium alcoholate $Ti(OR^4)_4$, preferably the isopropylate, isobutylate or n-butylate, is reacted with the higher alcohol $R^2OH$ (cf. equation III) at elevated temperatures (50-130° C.). The higher alcohol $R^2OH$ is used in a molar excess (as a rule from 1:5 to 1:20).

Equation III

$$Ti(OR^4)_4 + R^2OH \rightleftharpoons Ti(OR^2)_4 + R^4OH$$

$R^2$ cf. equation II $R^4$ is $C_1$-$C_8$-alkyl, preferably isopropyl, isobutyl or n-butyl $R^2OH$ and $R^4OH$ should preferably fulfill the following condition with regard to their boiling points bp.:

$bp. (R^2OH) \geq bp. (R^4OH) + 20°$ C.

Under these conditions, it is technically simple to keep the losses of $R^2OH$ small and to separate off $R^4OH$ as completely as possible.

The alcohol $R^4OH$ formed in the reaction is separated off by distillation or rectification, if necessary under reduced pressure. This can, if required, be supported by stripping with a suitable, unreactive gas. The resulting residue is the catalyst solution for the transesterification (Ti content: 2-10% by weight) and contains, as a rule, less than 400 ppm of $R^4OH$. Consequently, virtually no foreign alcohol ($R^4OH$) is introduced into the transesterification mixture (<100 ppm in the mixture).

However, it is of course also possible for the catalyst solution to contain mixed titanium alcoholates, depending on the reaction according to equation III.

With the use of a titanate, for example one prepared by the abovementioned method, the titanium content in the reaction mixture is as a rule 0.01-1% by weight.

The transesterification is carried out in one reactor or in a plurality of reactors connected in series, having at least one attached rectification column and condensers.

The reaction temperature is as a rule 80-140° C., preferably from 100 to 130° C., and the pressure is from 200 mbar to atmospheric pressure, preferably 300-800 mbar, particularly preferably from 400 to 600 mbar.

In the case of a plurality of reactors, the temperature in the various reactors may be identical or different, for example their increase or decrease, preferably increase, from one reactor to the other.

Heat can be supplied via wall heating and/or external or internal heat exchangers, for example tubular or plate heat exchangers, preferably via external circulation evaporators. The rectification columns are of known design and have internals having separation activity (for example bubble trays, Thormann trays, valve trays, sieve trays or dual-flow trays) or contain dumped or stacked packings. The condensers are likewise of known design and can be operated indirectly, for example as tubular or plate heat exchangers, or directly, for example as quench coolers. The uniform thorough mixing of the reaction solution is effected in a known manner, for example by stirring, pumped circulation or forced or natural circulation, preferably by forced or natural circulation.

The reaction zone and/or the heat exchangers installed in the plant, for example of the distillation units or reactors, is/are continuously flushed, according to the invention, with a gas or gas mixture which is inert under the reaction conditions, for example nitrogen, air, nitrogen/oxygen mixtures, argon, helium, carbon dioxide or carbon monoxide, preferably air or air/nitrogen mixtures, in particular those having an oxygen content of from 0.1 to 15, preferably from 0.5 to 10, % by volume and very particularly preferably those air/nitrogen mixtures having an oxygen content of from 1 to 5% by volume. The purge gas is preferably passed through the reaction mixture or along the heat exchanger surfaces present, particularly preferably in a forced or natural circulation evaporator present.

For this purpose, the purge gas is metered in, with pressure or volume regulation via suitable feed apparatus known per se and not restricted, in the vicinity of the heat exchanger surface present, so that the, preferably continuous, purge gas stream is fed countercurrently or cocurrently relative to the liquid along the heat exchanger surface.

The purge gas can be preheated to the temperature of the heat exchanger medium so that the temperature of the purge gas differs, for example, by not more than 15° C., preferably not more than 10° C., from the temperature of the heating medium.

In each case 0.1-100, preferably 0.2-80, particularly preferably 0.5-70, in particular 1-50, parts by volume, based on the volume of the reaction mixture (=1 part by volume) in the reactors and postreactors in the reaction zone, of purge gas are passed per hour through the heat exchangers or the reaction zone.

Particularly preferably, the purge gas is passed via the heat exchangers in which the reaction medium in the reactors or in the distillation columns is heated.

A particular embodiment of the novel transesterification comprises carrying out the reaction in at least one reactor with attached column and passing the reaction mixture continuously into a postreactor which is connected on the gas side to a transesterification reactor, preferably the last transesterification reactor, or to the attached column.

The temperature in the postreactor is as a rule 1-10° C. higher than in the reactor.

The residence time in the reaction zone, comprising the reactor(s) and, if required, the postreactor(s), is 1-4, preferably 1.5-3, hours.

The column(s) attached to the reactor(s) has/have as a rule 10-30 theoretical plates. The reflux ratio is as a rule 5-20:1, preferably 7-15:1. The conditions of this distillation are generally chosen so that the butanol fraction at the top of the column attached to the reactor contains 5-30%, preferably 10-20%, of n-butyl (meth)acrylate. As a rule, not more than 1, preferably not more than 0.5, particularly preferably not more than 0.3, % by weight of the higher alcohol $R^2OH$ is present.

The lower alcohol $R^1OH$ liberated during the transesterification is separated off together with a part of the lower (meth)acrylate I via the top of the rectification columns attached to the reactors.

The distillation conditions, for example the theoretical plates and the reflux ratio, are preferably chosen so that a nonazeotropic mixture is taken off at the top of the column, in which mixture the content of lower (meth)acrylate I is higher compared with the azeotropic composition comprising lower alkanol $R^1OH$ and lower (meth)acrylate I under the corresponding conditions.

The distillate can be recycled directly, i.e. without an additional purification step, into the synthesis of n-butyl (meth)acrylate, where it can be reacted with (meth)acrylic acid again to give the starting ester I, as described in the German Patent Application with the title Preparation of (meth)acrylates, with the same date of filing as the present document and the Application number 101 27 941.8. Advantageously, it can be fed there to the working-up process, particularly preferably to an extraction process.

The columns can be stabilized using the conventional stabilizers or mixtures thereof, for example N-oxyls, such as 4-hydroxy-2,2,6,6-tetramethylpiperidin-N-oxyl or 4-oxo-2,2,6,6-tetramethylpiperidin-N-oxyl, phenols and naphthols, such as p-aminophenol, p-nitrosophenol, 2-tert-butylphenol, 4-tert-butylphenol, 2,4-di-tert-butylphenol, 2-methyl-4-tert-butylphenol, 4-methyl-2,6-tert-butylphenol (2,6-tert-butyl-p-cresol) or 4-tert-butyl-2,6-dimethylphenol, quinones, such as hydroquinone or hydroquinone monomethyl ether, aromatic amines, such as N,N-diphenylamine, phenylenediamines, such as N,N'-dialkyl-para-phenylenediamine, it being possible for the alkyl radicals to be identical or different and in each case, independently of one another, to be of 1 to 4 carbon atoms and to be straight-chain or branched, hydroxylamines, such as N,N-diethylhydroxylamine, phosphorus-containing compounds, such as triphenylphosphine, triphenyl phosphite or triethyl phosphite, or sulfur-containing compounds, such as diphenyl sulfide or phenothiazine.

Furthermore, degradation products or derivatives of stabilizers may also be used, for example the Michael adduct of (meth)acrylic acid or (meth)acrylates and hydroquinone.

The stabilization can be effected in the presence or absence of molecular oxygen, preferably in the presence thereof.

The stabilization is preferably effected using phenothiazine, hydroquinone, hydroquinone monomethyl ether, 4-hydroxy-2,2,6,6-tetramethylpiperidin-N-oxyl, 4-oxo-2,2,6,6-tetramethylpiperidin-N-oxyl, 2,6-tert-butyl-p-cresol or mixtures thereof in amounts of, in each case, from 10 to 5000 ppm, particularly preferably phenothiazine or a phenothiazine-containing mixture, in particular a phenothiazine/4-hydroxy-2,2,6,6-tetramethylpiperidin-N-oxyl mixture, being used for the stabilization. The addition can be effected in each case by the starting materials, directly or via the recycle or reflux streams.

In particular, the stabilization is effected using the reflux to which 100-1000 ppm of phenothiazine and 10-500 ppm of 4-hydroxy-2,2,6,6-tetramethylpiperidin-N-oxyl have been added.

The stabilization is preferably effected using a solution of this stabilizer mixture in the lower (meth)acrylate.

Particularly preferably, the dissolved stabilizer mixture is sprayed onto the condenser surfaces.

The reaction mixture formed is discharged from the reactor, preferably continuously, and separated in a distillation unit (catalyst removal) into a top product, which mainly contains the desired ester and the starting materials, and a bottom product, which substantially contains desired ester, catalyst, high-boiling byproducts and polymerization inhibitors. The bottom product can be recycled at least partly, preferably in an amount of from 50 to 100%, into the first reactor. Any residue present can be subjected, for example, to a residue treatment.

The distillation unit may consist, for example, of a conventional forced or natural circulation evaporator and a column, for example having 5-15 theoretical plates, of conventional design. The rectification columns of the novel process are of known design and have internals having separation activity (for example bubble trays, Thormann trays, valve trays, sieve trays or dual-flow trays) or contain dumped or stacked packings.

According to the invention, the evaporator surfaces of the catalyst removal stage may also be flushed with a purge gas as described above.

The bottom temperature is, as a rule, 80-160° C., preferably 90-150° C., particularly preferably 90-120° C., and the corresponding pressure is 20-500, preferably 50-300, particularly preferably 80-150, mbar. The reflux ratio is as a rule 5:1-1:5, preferably 3:1-1:3, particularly preferably from 2:1 to 1:2.

The distillation can also be carried out at a higher temperature in order to cleave Michael adducts, as described in the German Patent Application with the title Preparation of (meth)acrylates with the same date of filing as the present document and the Application number 101 27 939.6.

If required, the distillation process can be supported by passing through a gas stream as described above which is substantially inert under the reaction conditions (stripping), e.g. nitrogen, as well as an oxygen-containing gas, such as air or air/nitrogen mixtures, in particular those having an oxygen content of from 0.1 to 15, preferably from 0.5 to 10, % by volume and very particularly preferably those air/nitrogen mixtures which have an oxygen content of from 1 to 5% by volume. The passage of the purge gas according to the invention is preferably associated with the stripping process.

In order to prevent polymer formation in the distillation unit, advantageously an about 0.1 to 1% strength solution of phenothiazine in the starting ester is sprayed into the condensers. The stabilization is preferably effected using the reflux to which 100-1000 ppm of phenothiazine and 10-500 ppm of 4-hydroxy-2,2,6,6-tetramethylpiperidin-N-oxyl have been added.

Particularly preferably, the dissolved stabilizer mixture is sprayed onto the condenser surfaces.

The distillate containing the desired ester and obtained in the catalyst removal can be separated in a further distillation unit (purifying distillation) into a low boiler fraction, which mainly comprises the starting materials and can be recycled into the transesterification, into a high boiler fraction (bottom product), which mainly contains desired ester and inhibitors and is advantageously recycled into the first distillation unit but can also be partly fed to the residue treatment, and into a medium boiler fraction, which substantially contains the desired ester. The desired ester is discharged, preferably in gaseous form, via a side take-off in the lower column region, preferably in the lower half, particularly preferably in the lower third, and is condensed. The desired ester is stabilized with 10-20 ppm of hydroquinone monomethyl ether or 2,6-tert-butyl-p-cresol, preferably by spraying onto the condenser in the gaseous side take-off.

The column has, as a rule, 10-30 theoretical plates.

The condensers and evaporators are likewise of known design, as described above, for example tubular or plate heat exchangers.

Heating is effected in a manner which is likewise known, preferably by natural or forced circulation.

According to the invention, the evaporator surfaces in the purifying distillation can also be flushed with a purge gas as described above.

The bottom temperature is as a rule 80-150° C., preferably 80-140° C., particularly preferably 90-130° C., and the corresponding pressure is 20-500, preferably 30-300, particularly preferably 40-200, mbar. The reflux ratio is from 5:1 to 1:15, preferably from 2:1 to 1:10.

The low boiler fraction not used as reflux can be recycled completely or partly into the transesterification, directly into a reactor or via a column attached thereto.

From 50 to 100%, preferably from 75 to 100%, particularly preferably from 90 to 100%, of the bottom product can be recycled into the catalyst removal. The remainder can be passed into the residue treatment.

In order to prevent polymer formation in the distillation units, a solution of about 0.5% of phenothiazine and 0.05% of 4-hydroxy-2,2,6,6-tetramethylpiperidin-N-oxyl in the starting ester is advantageously sprayed onto the condensers. The stabilization is preferably effected using the reflux to which 100-1000 ppm of phenothiazine and 10-500 ppm of 4-hydroxy-2,2,6,6-tetramethylpiperidin-N-oxyl have been added.

A particular embodiment of the process comprises subjecting the bottom discharge of the catalyst removal or, if required, a part thereof and, if required, of the purifying distillation to a continuous or batchwise thermal treatment (cleavage, distillation). This residue treatment in which desired ester still present is recovered and simultaneously the Michael adducts are cleaved into the corresponding alcohols and (meth)acrylates and are separated off is not limited.

The residue treatment can be operated continuously or batchwise in at least one reactor, if required with an attached column, but is preferably operated continuously.

In the residue treatment, for example, Michael adducts and polymers are cleaved.

These Michael adducts are in general cleavable into their starting compounds, for example by thermal and/or catalytic treatment, e.g. in the presence of a suitable catalyst.

The stream fed to the residue treatment can be thermally treated, with or without the addition of further, for example basic or acidic, catalysts, for cleavage of the Michael adducts present.

The temperature in the residue treatment is in general from 100 to 220° C., preferably from 120 to 200° C., particularly preferably from 140 to 180° C., in particular from 150 to 180° C.

The removal of the low boilers from the residue treatment can be supported by passing through a gas stream which is substantially inert under the reaction conditions (stripping), e.g. nitrogen as well as an oxygen-containing gas, such as air or air/nitrogen mixtures.

In this way, in general 50% or more of the useful products present (desired ester and starting materials) can be recovered.

The useful products separated off can then be recycled to the transesterification reactor, if required via an attached column, preferably to the catalyst removal or purifying distillation.

Consequently, no special, technically complicated measures are necessary for minimizing the formation of the Michael adducts during the synthesis and/or during the working-up.

The residue of the residue treatment can then be fed again to a residue treatment or can be disposed of in a suitable manner, for example by incineration.

Instead of a residue treatment, the bottom products of the process can of course also be disposed of without treatment.

The basic (meth)acrylate obtained by the process described has a purity of 99.9% or more, according to gas chromatographic analysis.

The content of saturated secondary components is as a rule <400 ppm, and that of N,N'-dimethylpiperazine, ethylene glycol di(meth)acrylate and vinyloxyethyl (meth)acrylate <100 ppm.

Advantages of the Process:
   The process can be operated completely continuously and requires not more than 3 distillation columns, or four with residue treatment. The capital costs and maintenance/repair costs are therefore relatively low.
   Industrial n-butyl (meth)acrylate can be used without difficulties in the plant or quality problems occurring.
   The novel process gives a high yield, i.e. small amounts of residue and hence little environmental pollution and low production costs.
   High purity, i.e. low content of byproducts and hence excellent further processing properties.

The dialkylaminoalkyl (meth)acrylates prepared according to the invention, in particular dialkylaminoethyl (meth)acrylates and especially dimethylaminoethyl (meth)acrylates are useful monomers for the preparation of copolymers. They are used as monomers as such or after quaternization in the polymerization.

Conventional quaternizing agents are, for example, benzyl halides, e.g. benzyl chloride, alkyl halides, e.g. methyl chloride, ethyl chloride, methyl bromide, ethylene dichloride or allyl chloride, alkylene oxides, e.g. ethylene oxide, propylene oxide, styrene oxide, isobutylene oxide or vinyloxirane, preferably ethylene oxide or propylene oxide and particularly preferably ethylene oxide, alkyl phosphites or phosphonates, e.g. trimethylphosphite or triethylphosphite, dialkyl sulfates, e.g. dimethyl sulfate or diethyl sulfate, dialkyl carbonates, e.g. dimethyl carbonate, diethylcarbonate or di-n-butyl carbonate, chlorohydrin or epichlorohydrin.

In particular, those copolymers which contain quaternized monomers in the form of polymerized units are used in the treatment of water, for example as ion exchange resins or as a component of membranes.

The example which follows illustrates the novel process without restricting it.

ppm and percentage data used in this document are by weight, unless stated otherwise.

EXAMPLE 1

134 g of dimethylaminoethanol, 175 g of n-butyl acrylate (purity 99.6%, 0.1% of dibutyl ether, 0.05% of butyl acetate, 0.03% of butyl propionate, 0.04% of water, 0.1% of isobutyl acrylate, 0.01% of acrylic acid and 0.02% of pentyl acrylates), 6 g of titanium tetrabutylate, 71 g of recycled catalyst and 833 g of recycled stream from the purifying distillation, which substantially comprised n-butyl acrylate (about 75%) and dimethylaminoethanol (about 17%) were fed per hour in a continuous operation, to a transesterification apparatus which consisted of a transesterification reactor (effective volume 1.8 l) with external circulation evaporator and attached distillation column (20 dual-flow trays) with condenser and a postreactor (effective volume 1.2 l) with external circulation evaporator. The temperature in the reactor was 120° C. and that in the postreactor 123° C. An n-butanol fraction which mainly comprised butanol (83%) and butyl acrylate (17%) was separated off via the top of the column and was condensed. 132 g of the condensate were discharged and the remainder (about 1400 g) was applied as reflux to the uppermost column tray. 15 g per hour of a solution of 0.5% of phenothiazine in n-butyl acrylate were sprayed onto the top of the condenser. In each case 10 l of air/h were blown into the circulation evaporator. The residence time was 2.6 hours.

The discharge of the postreactor was fed to a distillation unit which consisted of a distillation column (8 dual-flow trays) with circulation evaporator and condenser (bottom temperature 105° C.), and the high boilers (85 g/h), mainly comprising desired ester (about 65%), tetra(dimethylaminoethyl) titanate (about 30%) and n-butyl acrylate (about 3%), was separated off, about 80% being recycled into the esterification reactor and the remainder (17 g/h) being discharged. The product mixture (about 60% of n-butyl acrylate, about 13% of dimethylaminoethanol, about 25% of desired ester and about 2.5% of n-butanol) obtained at the top of the column (69° C./50 mbar) was condensed and partly (50%) applied as reflux again to the top of the column. For stabilization, a solution (15 g/h) of 0.5% of phenothiazine in n-butyl acrylate was sprayed into the condenser. The remainder of the distillate (about 1030 g/h) was fed to a further distillation unit which consisted of a column having 22 dual-flow trays with side take-off, condenser and circulation evaporator. A mixture of about 16.7% of dimethylaminoethanol, about 75% of n-butyl acrylate, about 5% of desired ester and about 3% of n-butanol was separated off at the top of the column and was partly (about 40%) applied as reflux again at the top of the column and partly (833 g/h) recycled into the transesterification reactor. The stabilization was effected using a solution of 0.5% of phenothiazine and 0.05% of 4-hydroxy-2,2,6,6-tetramethyl-piperidin-N-oxyl. The bottom product (about 10 g/h), mainly desired ester (about 99%), was fed to the catalyst removal. The dimethylaminoethyl acrylate separated off in gaseous form via the side take-off was condensed (206 g/h) and was stabilized with about 20 ppm of hydroquinone monomethyl ether.

In each case 10 l/h of air were passed into the circulation evaporators of the two distillation units.

The yield of distilled product was 96% (based on dimethylaminoethanol). The purity determined by gas chromatography was 99.9%, <20 ppm of dimethylaminoethanol, about 100 ppm of butyl acrylate, about 250 ppm of water, about 300 ppm of dimethylaminoethyl propionate and <10 ppm of dibutyl ether being found as secondary components.

N,N'-Dimethylpiperazine, ethylene glycol di(meth)acrylate and vinyloxyethyl (meth)acrylate were not detectable.

The plant was operated for 30 days without polymer problems.

EXAMPLE 2

As Comparison

The procedure was as in example 1, but without purge gas in the circulation evaporators and heat exchangers.

In the course of 5 days, the content of dimethylpiperazine in the desired ester increased to about 100 ppm and that of vinyloxyethyl acrylate to about 20 ppm. After 7 days, the apparatus had to be shut down owing to fouling of the heat exchanger pipes with polymer.

EXAMPLE 3

The effect of the residence time on the formation of byproducts (Michael adducts and N,N'-dimethylpiperazine) in the reactor discharge was investigated.

The procedure corresponded to the transesterification process described in example 1. The discharge was analyzed by gas chromatography after the catalyst had been separated off by hydrolysis and filtration.

| Residence time | Michael adduct | N,N'-Dimethylpiperazine |
|---|---|---|
| 2 hours | 2.5% | 0.8% |
| 3 hours | 4.6% | 1.5% |
| 5 hours | 6.0% | 2.5% |
| 7 hours | 6.9% | 3.1% |

EXAMPLE 4

The procedure was analogous to example 1 but the residence time was set at 5 hours.

A yield of 93%, based on dimethylaminoethanol, was obtained and the content of N,N'-dimethylpiperazine in the desired ester was 60 ppm.

COMPARATIVE EXAMPLE 1

With continuous operation, 680 parts of dimethylaminoethanol, 2016 parts of a mixture of ethyl acrylate and the distillate of ethyl acrylate removal, 70 parts of catalyst solution from example 1 and 110 parts of recycled catalyst (bottom product of the catalyst removal) were fed per hour to the first reactor of a reactor cascade consisting of two reactors. The reactors were each equipped with an attached packed column and a condenser. Heat was supplied via external heat exchangers. In addition, 236 parts per hour of the condensate of the low boiler removal were added via a feed in the middle of the column of the first reactor. The discharge of the second reactor was fed to a container which was equipped with a circulation evaporator and connected on the gas side to the column of the second reactor. The reaction temperatures were 110 and 115° C., respectively, and the temperature in the container was 119° C. The ethanol formed in the transesterification was discharged as a mixture with ethyl acrylate (48% of ethanol) at the top of the reactor columns and as condensed. The combined condensates were partly recycled as reflux into the columns (in each case about 2100 parts) and the remainder (806 parts) was discharged and collected for use in the ethyl acrylate preparation. The condensates were stabilized by adding 120 parts of a solution of 0.5% of phenothiazine and 0.05% of 4-hydroxy-2,2,6,6-tetramethylpiperidin-N-oxyl in ethyl acrylate to each condenser. The combined condensates contained about 48% by weight of ethanol and about 52% by weight of ethyl acrylate, and the dimethylaminoethanol content was less than 0.1%.

The discharge of the container was fed to a packed column (fed in the middle of the column), where it was separated into a top product (top temperature 88° C., 500 mbar) and a catalyst-containing bottom product (bottom temperature 140° C.).

The top product was stabilized by spraying 110 parts of the stabilizer solution described above into the top of the condenser. The condensate was mixed with 1170 parts of ethyl acrylate and partly (380 parts/hour) recycled as reflux to the column and the remainder (2016 parts/hour) was fed to the first reactor.

The bottom product was fed to a flash evaporator which was additionally equipped with a circulation evaporator (135° C., 80 mbar). The distillate was stabilized with 50 parts of stabilizer solution (see above) and contained about 90% of dimethylaminoethyl acrylate. The bottom product was partly (110 parts) fed to the first reactor and the remainder (70 parts/hour) was fed to the residue treatment.

The ratio of the Michael adduct formation (EP-A 906 902, page 9), calculated over both distillation stages, was negative (−1.3%), which means a partial reduction (cleavage) of the adducts under said conditions.

The further working-up of the distillate of the flash evaporation was carried out analogously to example 2 and gave 1189 parts of dimethylaminoethyl acrylate with a purity of 99.9%, which corresponds to a yield of 97.9%, based on dimethylaminoethanol.

COMPARATIVE EXAMPLE 2

The procedure was analogous to comparative example 1 but the bottom temperature in the ethyl acrylate removal was 110° C. and the temperature in the catalyst removal (flash evaporator) was 110° C.

The ratio of Michael adduct formation determined on the basis of the gas chromatographic analyses of the individual streams was +0.1%, i.e. there was a slight increase in the Michael adduct.

We claim:

1. A process for preparing basic (meth)acrylates, comprising:
    transesterifying a lower alkyl (meth)acrylate with a basic alcohol in the presence of a catalyst in a reactor of a reactor system comprising at least one distillation column, wherein the reactor is continuously flushed with a purge gas of a gas or gas mixture that is inert to the reactants in the reactor; and
    distilling the (meth)acrylate transesterification product obtained to prepare a purified basic (meth)acrylate;
    where, upon distillation, a nonazeotropic mixture is formed and removed from the top of the at least one distillation column, in which mixture the content of lower alkyl (meth)acrylate is greater compared to an azeotropic mixture that is formed and is comprised of a lower alkanol $R^1OH$ and a lower alkyl(meth)acrylate that is removed from the at least one distillation column; and wherein said purified basic (meth)acrylate is removed by distillation in gaseous form from a side position of the at least one distillation column.

2. The process as claimed in claim 1, wherein the purge gas of a gas or gas mixture that is inert to the reactants in the reactor is air or a mixture of air and nitrogen.

3. The process as claimed in claim 1, wherein the reactor system comprising at least one distillation column, further comprises at least one post reactor, circulation evaporator or combination thereof.

4. The process as claimed in claim 1, wherein a residence time of the reactants in the reactor in the reactor system comprising at least one distillation column ranges from 1.5 to 3 hours.

5. The process as claimed in claim 1, wherein the transesterification is conducted in the presence of a titanium tetraalcoholate, the alcoholate corresponding to the alcohol component of the lower alkyl (meth)acrylate.

6. The process as claimed in claim 1, wherein a reaction mixture obtained from the reaction is stabilized by the presence of phenothiazine stabilizer or a mixture of phenothiazine with at least one other stabilizer.

7. The process as claimed in claim 6, wherein the at least one other stabilizer is 4-hydroxy-2,2,6,6-tetramethylpiperidin-N-oxyl.

8. The process as claimed in claim 1, wherein at least a part of distillation bottom products obtained upon distillation is subjected to catalyst removal.

9. The process as claimed in claim 1, wherein the lower alkyl (meth)acrylate is selected from the group consisting of methyl (meth)acrylate, ethyl (meth)acrylate, n-propyl (meth)acrylate, isopropyl (meth)acrylate, n-butyl (meth)acrylate, isobutyl (meth)acrylate, sec-butyl (meth)acrylate, tert-butyl (meth)acrylate, n-pentyl (meth)acrylate and n-hexyl (meth)acrylate.

10. The process as claimed in claim 9, wherein the lower alkyl (meth)acrylate is n-butyl (meth)acrylate.

11. The process as claimed in claim 10, wherein the n-butyl (meth)acrylate is of industrial purity.

12. The process as claimed in claim 1, wherein the basic (meth)acrylate is selected from the group consisting of 2-dimethylaminoethyl (meth)acrylate, 3-dimethylaminopropyl (meth)acrylate, 1-dimethylaminoprop-2-yl (meth)acrylate, 2-dimethylaminopropyl (meth)acrylate, 6-dimethylaminoethyl (meth)acrylate, 2-diethylaminoethyl (meth)acrylate, 3-diethylaminopropyl (meth)acrylate, 6-diethylaminohexyl (meth)acrylate, 2-dibutylaminoethyl (meth)acrylate, 3-dibutylaminopropyl (meth)acrylate and 6-dibutylaminohexyl (meth)acrylate.

13. The process as claimed in claim 12, wherein the basic (meth)acrylate is dimethylaminoethyl acrylate.

14. A process for preparing basic (meth)acrylates comprising:
   transesterifying a lower alkyl (meth)acrylate with a basic alcohol in the presence of a catalyst in a reactor of a reactor system comprising a reactor, at least one distillation column, circulation evaporators and a post reactor, wherein the reactor system is continuously flushed with a purge gas of a gas or gas mixture that is inert to the reactants in the reactor; and
   distilling the (meth)acrylate transesterification product obtained to prepare a purified basic (meth)acrylate;
   wherein the purge gas is flushed through the reactor system in an amount of 0.1 to 100 parts by volume based on 1 part by volume of reaction mixture in the reactor.

15. A process for preparing basic (meth)acrylates, comprising:
   transesterifying an alkyl (meth)acrylate with a basic alcohol in the presence of a catalyst in a reactor of a reactor system further comprising circulation evaporators, at least one distillation column and a post reactor, whereby the residence time of reaction mixture in the reactor and post reactor ranges from 1.5 to 3 hours and wherein at least one of the reactor, post reactor and circulation evaporators is continuously flushed with a purge gas of a gas or a gas mixture that is inert to the reactants in the reactor; and
   distilling the (meth)acrylate transesterification product obtained to prepare a purified basic (meth)acrylate.

* * * * *